United States Patent [19]
Mercurio et al.

[11] Patent Number: 5,972,674
[45] Date of Patent: Oct. 26, 1999

[54] STIMULUS-INDUCIBLE PROTEIN KINASE COMPLEX AND METHODS OF USE THEREFOR

[75] Inventors: Frank Mercurio; Hengyi Zhu; Miguel Barbosa, all of San Diego, Calif.

[73] Assignee: Signal Pharmaceuticals, Inc., San Diego, Calif.

[21] Appl. No.: 08/697,393

[22] Filed: Aug. 26, 1996

[51] Int. Cl.⁶ .................................................. C12N 9/12
[52] U.S. Cl. ......................... 435/194; 530/350; 530/352
[58] Field of Search ................................ 530/350, 352; 435/194

[56] References Cited

FOREIGN PATENT DOCUMENTS

WO 97/35014   9/1997   WIPO .

OTHER PUBLICATIONS

Connelly et al., Cellular and Molecular Biology Research, vol. 41: 537–549, Jun. 1995.
Regnier et al., Cell, vol. 90: 373–383, Jul. 1997.
Chen et al., vol. 84:853–862, Mar. 1996.
Mercurio et al., Faseb Journal, vol. 10: A1265, May 1996.
DiDonato et al., Molecular and Cellular Biology, vol. 16: 1295–1304, May 1996.
Barroga et al., "Constitutive phosphorylation of IκBα by casein kinase II," *Proc. Natl. Acad. Sci. USA* 92(17):7637–41, 1995.
Ghosh and Baltimore, "Activation in vitro of NF–κB by phosphorylation of its inhibitor IκB," *Nature* 344(6267):678–82, 1990.
Israël A., "IκB kinase all zipped up," *Nature* 388:519–521, 1997.
Kumar et al., "Double–stranded RNA–dependent protein kinase activates transcription factor NF–κB by phosphorylating IκB," *Proc. Natl. Acad. Sci. USA* 91)(14):6288–92, 1994.
Kuno et al., "Identification of an IκBα–associated Protein Kinase in a Human Monocytic Cell Line and Determination of Its Phosphorylation Sites on IκBα," *The Journal of Biological Chemistry* 270(46):27914–27919, 1995.
Maniatis, T., "Catalysis by a Multiprotein IκB Kinase Complex," *Science* 278:818–819, 1997.
Meco et al., "ζPKC induces phosphorylation and inactivation of IκB–α in vitro," *The EMBO Journal* 13(12):2842–8, 1994.

*Primary Examiner*—Christina Y. Chan
*Assistant Examiner*—Patrick J. Nolan
*Attorney, Agent, or Firm*—SEED and BERRY LLP

[57] ABSTRACT

Compositions and methods are provided for treating NF-κB-related conditions. In particular, the invention provides a stimulus-inducible IκBα kinase complex, and components and variants thereof. IκBα kinase complex may be used, for example, to identify antibodies and other agents that inhibit or activate signal transduction via the NF-κB cascade. IκBα kinase complex, components thereof and/or such agents may also be used for the treatment of diseases associated with NF-κB activation.

2 Claims, 6 Drawing Sheets

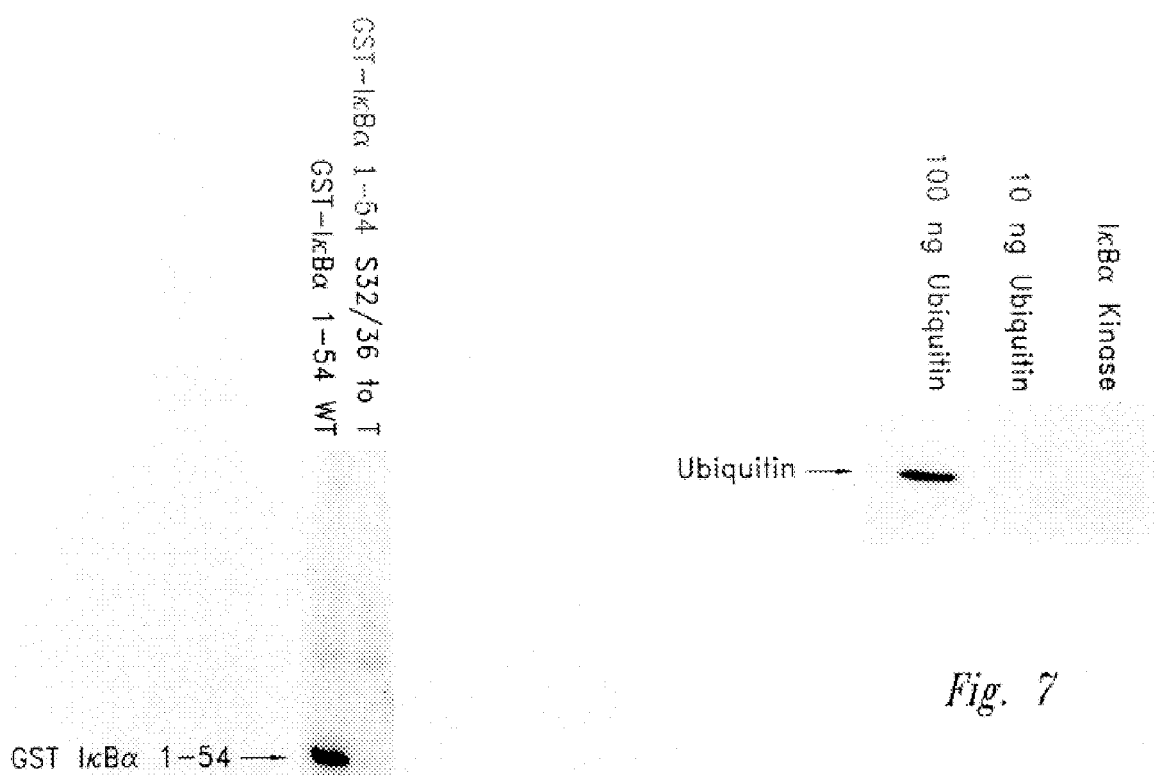

STIMULUS-INDUCIBLE PROTEIN KINASE COMPLEX AND METHODS OF USE THEREFOR

TECHNICAL FIELD

The present invention relates generally to compositions and methods useful for the study of cascades leading to the activation of nuclear factor κB (NF-κB) and for treating diseases associated with such pathways. The invention is more particularly related to a stimulus-inducible IκBα kinase complex, a component IκBα kinase and variants thereof that specifically phosphorylate IκBα at residues S32 and S36. The present invention is also related to the use of a stimulus-inducible IκBα kinase complex or IκBα kinase to identify antibodies and other agents that inhibit or activate signal transduction via the NF-κB pathway.

BACKGROUND OF THE INVENTION

NF-κB is a transcription factor that plays a pivotal role in the highly specific pattern of gene expression observed for immune, inflammatory and acute phase response genes, including interleukin 1, interleukin 8, tumor necrosis factor and certain cell adhesion molecules. Like other members of the Rel family of transcriptional activators, NF-κB is sequestered in an inactive form in the cytoplasm of most cell types. A variety of extracellular stimuli including mitogens, cytokines, antigens, stress inducing agents, UV light and viral proteins initiate a signal transduction pathway that ultimately leads to NF-κB release and activation. Thus, inhibitors and activators of the signal transduction pathway may be used to alter the level of active NF-κB, and have potential utility in the treatment of diseases associated with NF-κB activation.

An important modulator of NF-κB activation is the inhibitor protein IκBα, which associates with (and thereby inactivates) NF-κB in vivo. Stimulus-induced phosphorylation of IκBα at serine residues (S32 and S36) renders the inhibitor a target for ubiquitination and subsequent degradation by the proteosome, leading to NF-κB activation. The induction of IκBα phosphorylation is a critical step in NF-κB activation, and the identification of IκBα kinase, as well as proteins that modulate its kinase activity, would further the understanding of the activation process, as well as the development of therapeutic methods.

Several protein kinases have been found to phosphorylate IκBα in vitro, including protein kinase A (Ghosh and Baltimore, *Nature* 344:678–682, 1990), protein kinase C (Ghosh and Baltimore, *Nature* 344:678–682, 1990) and double stranded RNA-dependent protein kinase (Kumar et al., *Proc. Natl. Acad Sci. USA* 91:6288–6292, 1994). Constitutive phosphorylation of IκBα by casein kinase II has also been observed (see Barroga et al., *Proc. Natl. Acad. Sci USA* 92:7637–7641, 1995). None of these kinases, however appear to be responsible for in vivo activation of NF-κB. For example, phosphorylation of IκBα in vitro by protein kinase A and protein kinase C prevent its association with NF-κB, and phosphorylation by double-stranded RNA-dependent protein kinase results in dissociation of NF-κB. Neither of these conform to the effect of phosphorylation in vivo, where IκBα phosphorylation at S32 and S36 does not result in dissociation from NF-κB.

Other previously unknown proteins with IκBα kinase activity have been reported, but these proteins also do not appear to be significant activators in vivo. A putative IκBα kinase was identified by Kuno et al., *J Biol. Chem.* 270:27914–27919, 1995, but that kinase appears to phosphorylate residues in the C-terminal region of IκBα, rather than the S32 and S36 residues known to be important for in vivo regulation. Diaz-Meco et al., *EMBO J* 13:2842–2848, 1994 also identified a 50 kD IκB kinase, with uncharacterized phosphorylation sites. Finally, Chen et al, *Cell* 84:853–862, 1996 identified a kinase that phosphorylates IκBα, but that kinase was identified using a non-physiological inducer of IκBα kinase activity and requires the addition of exogenous factors for in vitro phosphorylation.

Accordingly, there is a need in the art for an IκBα kinase that possesses the substrate specificity and other properties of the in vivo kinase. There is also a need for improved methods for modulating the activity of proteins involved in activation of NF-κB, and for treating diseases associated with NF-κB activation. The present invention fulfills these needs and further provides other related advantages.

SUMMARY OF THE INVENTION

Briefly stated, the present invention provides compositions and methods employing a large, multi-subunit stimulus-inducible IκBα kinase complex, or a component or variant thereof. In one aspect, the present invention provides a stimulus-inducible IκBα kinase complex capable of specifically phosphorylating IκBα at residues S32 and/or S36 without the addition of exogenous cofactors.

In a related aspect, a component of a stimulus-inducible IκBα kinase complex is provided, wherein the component is capable of phosphorylating IκBα. An isolated DNA molecule and recombinant expression vector encoding such a component complex, as well as a transfected host cell, are also provided.

In another aspect, methods for preparing a stimulus-inducible IκBα kinase complex are provided, comprising combining components of a stimulus-inducible IκBα kinase complex in a suitable buffer.

In yet another aspect, methods are provided for phosphorylating a substrate of a stimulus-inducible IκBα kinase complex, comprising contacting a substrate with a stimulus-inducible IκBα kinase complex or a component thereof, and thereby phosphorylating the substrate.

In a further aspect, the present invention provides a method for screening for an agent that modulates IκBα kinase complex activity, comprising: (a) contacting a candidate agent with a stimulus-inducible IκBα kinase complex, wherein the step of contacting is carried out under conditions and for a time sufficient to allow the candidate agent and the stimulus-inducible IκBα kinase complex to interact; and (b) subsequently measuring the ability of said candidate agent to modulate IκBα kinase complex activity.

In another aspect, an antibody is provided that binds to a component of IκBα kinase complex capable of phosphorylating IκBα.

In further aspects, the present invention provides methods for modulating NF-κBα activity in a patient, comprising administering to a patient an agent that modulates IκBα kinase activity in combination with a pharmaceutically acceptable carrier. Methods are also provided for treating a patient afflicted with a disorder associated with the activation of IκBα kinase complex, comprising administering to a patient a therapeutically effective amount of an agent that modulates IκBα kinase activity in combination with a pharmaceutically acceptable carrier.

In yet another aspect, a method for detecting IκBα kinase complex activity in a sample is provided, comprising: (a)

contacting a sample with an antibody that binds to a stimulus-inducible IκBα kinase complex under conditions and for a time sufficient to allow the antibody to immunoprecipitate an IκBα kinase complex; (b) separating immunoprecipitated material from the sample; and (c) determining the ability of the immunoprecipitated material to specifically phosphorylate IκBα at residues S32 and/or S36.

In a related aspect, a kit for detecting IκBα kinase complex activity in a sample is provided, comprising an antibody that binds to IκBα kinase complex in combination with a suitable buffer.

In a further aspect, the present invention provides a method for identifying an upstream kinase in the NF-κB signal transduction cascade, comprising evaluating the ability of a candidate upstream kinase to phosphorylate a stimulus-inducible IκBα kinase complex or a component thereof or variant thereof.

A method for identifying a component of a stimulus-inducible IκBα kinase complex is also provided, comprising: (a) isolating a stimulus-inducible protein kinase complex; (b) separating said complex into components, and (c) obtaining a partial sequence of a component.

In yet another aspect, a method is provided for preparing a stimulus-inducible protein kinase complex from a biological sample, comprising: (a) separating a biological sample into two or more fractions; and (b) monitoring IκBα kinase complex activity in the fractions.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 3A shows the results employing an extract from cells that were not treated with TNFα, and FIG. 3B shows the results when the cells were treated with TNFα.

FIG. 6 is an autoradiogram showing the results of immunokinase assays performed using cytoplasmic extracts of TNFα-treated HeLa S3 cells following gel filtration. The assay was performed using the substrates GST-IκBα1–54 wildtype (lane 1) and GST-IκBα1–54 S32/36 to T (lane 2). The positions of IκBα and GST-IκBα 1–54 are indicated on the left.

FIG. 7 is an autoradiogram showing the results of a western blot analysis of the level of ubiquitin within a stimulus-inducible IκBα complex. Lane 1 shows the detection of 100 ng ubiquitin, Lane 2 shows 10 ng ubiquitin and Lane 3 shows 3.4 μg of IκBα kinase complex purified through the phenyl superose step (sufficient quantities for 10 kinase reactions). The position of ubiquitin is shown by the arrow on the left.

DETAILED DESCRIPTION OF THE INVENTION

As noted above, the present invention is generally directed to compositions and methods for modulating (i.e., stimulating or inhibiting) signal transduction leading to NF-κB activation. In particular, the present invention is directed to compositions comprising a stimulus-inducible IκBα kinase complex (also referred to herein as "IκBα kinase complex") that is capable of specifically phosphorylating IκBα at residues S32 and/or S36 without the addition of exogenous cofactors. The present invention also encompasses compositions that contain one or more components of such an IκBα kinase complex, or variants of such components. A preferred component, referred to herein as "IκBα kinase," is capable of phosphorylating IκBα.

A stimulus-inducible IκBα kinase complex, and/or IκBα kinase may generally be used for phosphorylating a substrate (such as IκBα or a portion or variant thereof) and for identifying modulators of IκBα kinase activity. Such modulators and methods employing them for modulating IκBα kinase activity, in vivo and/or in vitro, are also encompassed by the present invention. In general, compositions that inhibit IκBα kinase activity may inhibit IκBα phosphorylation, or may inhibit the activation of IκBα kinase and/or IκBα kinase complex.

Figure 2A:
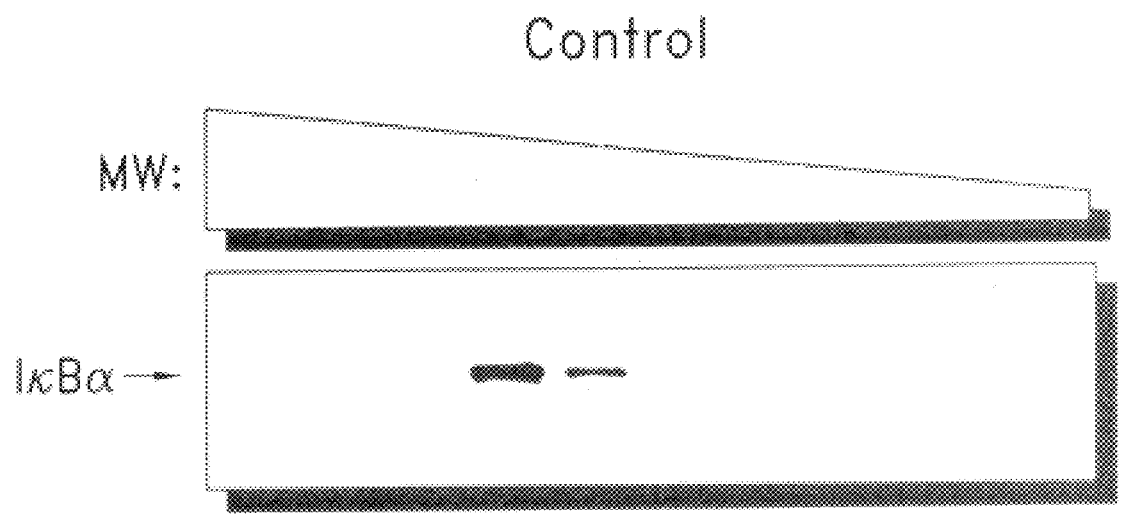
FIGS. 2A and 2B are autoradiograms that show the results of a Western blot analysis of the levels of IκBα in HeLa S3 cytoplasmic extracts following gel filtration. The extracts were prepared from cells that were (FIG. 2B) and were not (FIG. 2A) exposed to TNFα.
Figure 2B:
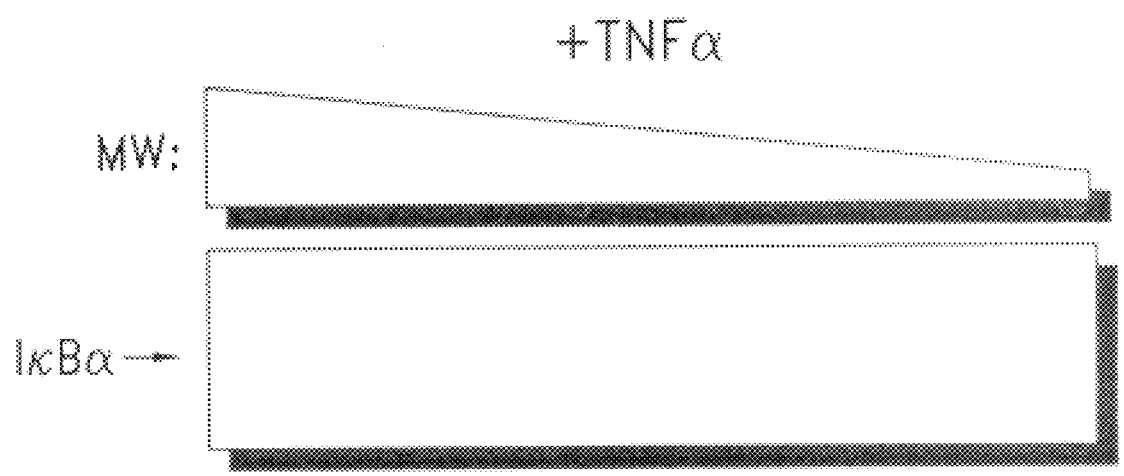

A stimulus-inducible IκBα kinase complex has several distinctive properties. Such a complex is stable (i.e., its components remain associated following purification as described herein) and has a high-molecular weight (about 700 kD, as determined by gel filtration chromatography). As shown in FIGS. 2 (A and B) and 3 (A and B), IκBα kinase activity of IκBα kinase complex is "stimulus-inducible" in that it is stimulated by TNFα (i.e., treatment of cells with TNFα results in increased IκBα kinase activity and IκBα degradation) and/or by one or more other inducers of NF-κB, such as IL-1, LPS, TPA, UV irradiation, antigens, viral proteins and stress-inducing agents. The kinetics of stimulation by TNFα correspond to those found in vivo. IκBα kinase activity of an IκBα kinase complex is also specific for S32 and/or S36 of IκBα. As shown in FIGS. 4 (A and B) and 5 (A and B), an IκBα kinase complex is capable of phosphorylating a polypeptide having the N-terminal sequence of IκBα (IκBα 1–54), but such phosphorylation cannot be detected in the IκBα derivative containing threonine substitutions at positions 32 and 36. A further characteristic of an IκBα kinase complex is its ability to phosphorylate a substrate in vitro in a standard kinase buffer, without the addition of exogenous cofactors. Free ubiquitin is not detectable in preparations of IκBα kinase complex (see FIG. 7), even at very long exposures. Accordingly the IκBα kinase complex differs from the ubiquitin-dependent IκBα kinase activity described by Chen et al., *Cell* 84:853–862, 1996.

IκBα kinase complex may be immunoprecipitated by antibodies raised against MKP-1 (MAP kinase phosphatase-1, Santa Cruz Biotechnology, Inc., Santa Cruz, Calif. #SC-1102) as determined by in vitro IκBα kinase assay. This suggests that MKP-1 may be a component of IκBα kinase complex. The substrate specificity of the immunoprecipitated IκBα kinase complex is maintained (i.e., there is strong phosphorylation of wildtype GST-IκBα 1–54, and substantially no detectable phosphorylation of GST-IκBα S32/36 to T substrate).

Figure 1:
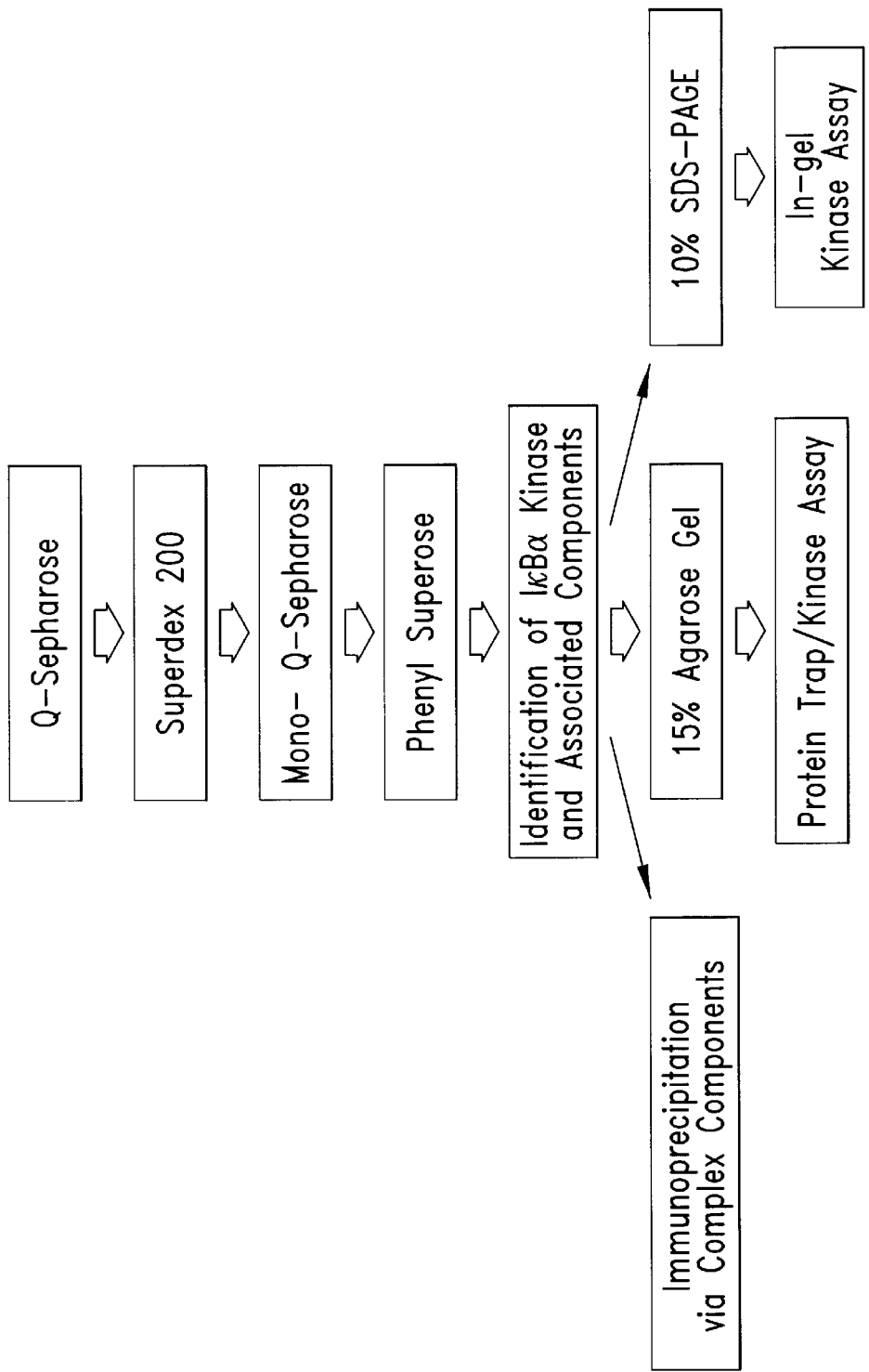
FIG. 1 is a flow chart depicting a purification procedure for the preparation of IκBα kinase.

An IκBα kinase complex may be isolated from human or other cells, and from any of a variety of tissues and/or cell types. For example, using standard protocols, cytoplasmic and/or nuclear/membrane extracts may be prepared from HeLa S3 cells following seven minutes induction with 30 ng/mL TNFα. The extracts may then be subjected to a series of chromatographic steps that includes Q Sepharose, gel filtration (HiLoad 16/60 Superdex 200), Mono Q, Phenyl Superose, gel filtration (Superdex 200 10/30) and Mono Q. This representative purification procedure is illustrated in FIG. 1, and results in IκBα kinase complex purified to near homogeneity (compare, for example, FIGS. 4A and 5A).

Throughout the fractionation, an in vitro kinase assay may be used to monitor the IκBα kinase activity of the IκBα kinase complex. In such an assay, the ability of a fraction to phosphorylate an appropriate substrate (typically IκBα or a derivative or variant thereof) is evaluated by any of a variety of means apparent to those of ordinary skill in the art. For example, a substrate may be combined with a chromatographic fraction in a protein kinase buffer containing $^{32}P$ γ-ATP, phosphatase inhibitors and protease inhibitors. The mixture may be incubated for 30 minutes at 30° C. The reaction may then be stopped by the addition of SDS sample buffer and analyzed using SDS-PAGE with subsequent autoradiography. Suitable substrates include full length IκBα, as well as polypeptides comprising the N-terminal 54 amino acids of IκBα, with or without an N-terminal tag. A suitable substrate is a protein containing residues 1–54 of IκBα and an N-terminal GST tag (referred to herein as GST-IκBα 1–54). To evaluate the specificity of an IκBα kinase complex, IκBα mutants containing threonine or alanine residues at positions 32 and 36, and/or other modifications, may be employed.

Alternatively, an IκBα kinase complex may be prepared from its components, which are also encompassed by the present invention. Such components may be produced using well known recombinant techniques, as described in greater detail below. Components used to prepare IκBα kinase complex may be native, or may be variants of the native component (i.e., a component sequence may differ from the native sequence in one or more conservative substitutions and/or modifications, provided that the ability of a complex comprising the component variant to specifically phosphorylate IκBα is not substantially diminished). Such substitutions, which are preferably conservative, may be made in non-critical and/or critical regions of the native protein. Component variants may also, or alternatively, contain other modifications, including the deletion or addition of amino acids that have minimal influence on the activity of the polypeptide. In particular, variants may contain additional amino acid sequences at the amino and/or carboxy termini. Such sequences may be used, for example, to facilitate purification or detection of the component polypeptide.

A component may generally be prepared from a DNA sequence that encodes the component using well known recombinant methods. DNA sequences encoding components of an IκBα kinase complex may be isolated by, for example, screening a suitable expression library (i.e., a library prepared from a cell line or tissue that expresses IκBα kinase, such as spleen, leukocytes, HeLa cells or Jurkat cells) with antibodies raised against IκBα kinase or against one or more components thereof. Protein components may then be prepared by expression of the identified DNA sequences, using well known recombinant techniques.

Alternatively, partial sequences of the components may be obtained using standard biochemical purification and microsequencing techniques. For example, purified complex may be run on an SDS-PAGE gel and individual bands may be isolated and subjected to protein microsequencing. DNA sequences encoding components may then be prepared by amplification from a suitable human cDNA library, using polymerase chain reaction (PCR) and methods well known to those of ordinary skill in the art. For example, an adapter-ligated cDNA library prepared from a cell line or tissue that expresses IκBα kinase (such as HeLa or Jurkat cells) may be screened using a degenerate 5' specific forward primer and an adapter-specific primer. Degenerate oligonucleotides may also be used to screen a cDNA library, using methods well known to those of ordinary skill in the art. In addition, known proteins may be identified via Western blot analysis using specific antibodies.

Components of a IκBα kinase complex may also be identified by performing any of a variety of protein-protein interaction assays known to those of ordinary skill in the art. For example, MKP-1 or other components can be used as "bait" in standard two-hybrid screens to identify other regulatory molecules such as, perhaps, NFκB1, Re1A, IκBβ and/or p70 S6 kinase (Kieran et al., *Cell* 62:1007–1018, 1990; Nolan et al., *Cell* 64:961–969, 1991; Thompson et al., *Cell* 80:573–582, 1995; Grove et al., *Mol. Cell. Biol.* 11:5541–5550, 1991).

A particularly preferred component of IκBα kinase complex is IκBα kinase. IκBα kinase may be identified based upon its ability to phosphorylate IκBα, which may be readily determined using the representative kinase assays described herein. As noted above, IκBα kinase within an IκBα kinase complex specifically phosphorylates IκBα at residues S32 and S36. Isolated IκBα kinase may, but need not, display such specific phosphorylation.

A component of IκBα kinase complex may generally be prepared from DNA encoding the component by expression of the DNA in cultured host cells. Preferably, the host cells are bacteria, yeast, baculovirus-infected insect cells or mammalian cells. The recombinant DNA may be cloned into any expression vector suitable for use within the host cell, using techniques well known to those of ordinary skill in the art. An expression vector may, but need not, include DNA encoding an epitope, such that the recombinant protein contains the epitope at the N- or C-terminus. Epitopes such as glutathione-S transferase protein (GST), HA (hemagglutinin)-tag, FLAG and Histidine-tag may be added using techniques well known to those of ordinary skill in the art.

The DNA sequences expressed in this manner may encode native components of IκBα kinase complex, or may encode portions or variants of native components. DNA molecules encoding variants may generally be prepared using standard mutagenesis techniques, such as oligonucleotide-directed site-specific mutagenesis. Sections of the DNA sequence may also, or alternatively, be removed to permit preparation of truncated polypeptides and DNA encoding additional sequences such as "tags" may be added to the 5' or 3' end of the DNA molecule.

Components of IκBα kinase complex may generally be used to reconstitute IκBα kinase complex. Such reconstitution may be achieved by combining IκBα kinase complex components in a suitable buffer.

Expressed IκBα kinase complex, or components thereof, is generally isolated in substantially pure form. Preferably, IκBα kinase complex and its components are isolated to a purity of at least 80% by weight, more preferably to a purity of at least 95% by weight, and most preferably to a purity of at least 99% by weight. In general, such purification may be achieved using, for example, the representative purification method described herein or the standard techniques of ammonium sulfate fractionation, SDS-PAGE electrophoresis, and affinity chromatography. IκBα kinase and components for use in the methods of the present invention may be native, purified or recombinant.

In one aspect of the present invention, an IκBα kinase complex and/or components thereof may be used to identify modulating agents, which may be antibodies (e.g., monoclonal), polynucleotides or other drugs, that inhibit or stimulate signal transduction via the NF-κB cascade. Modulation includes the suppression or enhancement of NF-κB activity. Modulation may also include suppression or enhancement of IκBα phosphorylation or the stimulation or inhibition of the ability of activated (i.e., phosphorylated) IκBα kinase complex to phosphorylate a substrate. Compositions that inhibit NF-κB activity by inhibiting IκBα phosphorylation may include one or more agents that inhibit or block IκBα kinase activity, such as an antibody that neutralizes IκBα kinase complex, a competing peptide that represents the substrate binding domain of IκBα kinase or the phosphorylation motif of IκBα, an antisense polynucleotide or ribozyme that interferes with transcription and/or translation of IκBα kinase, a molecule that inactivates IκBα kinase complex by binding to the complex, a molecule that binds to IκBα and prevents phosphorylation by IκBα kinase complex or a molecule that prevents transfer of phosphate groups from the kinase to the substrate.

In general, modulating agents may be identified by combining a test compound with an IκBα kinase complex, IκBα kinase or a polynucleotide encoding IκBα kinase) in vitro or in vivo, and evaluating the effect of the test compound on the IκBα kinase activity using, for example, a representative assay described herein. An increase or decrease in kinase activity can be measured by adding a radioactive compound, such as $^{32}$P-ATP and observing radioactive incorporation into a suitable substrate for IκBα kinase complex, thereby determining whether the compound inhibits or stimulates kinase activity. Briefly, a candidate agent may be included in a reaction mixture containing compounds necessary for the kinase reaction (as described herein) and IκBα substrate, along with IκBα kinase complex, IκBα kinase or polynucleotide encoding IκBα kinase. In general, a suitable amount of antibody or other agent for use in such an assay ranges from about 0.01 μM to about 10 μM. The effect of the agent on IκBα kinase activity may then be evaluated by quantitating the incorporation of [$^{32}$P]phosphate into IκBα, and comparing the level of incorporation with that achieved using IκBα kinase without the addition of a candidate agent. Alternatively, the effect of a candidate modulating agent on transcription of IκBα kinase may be measured, for example, by Northern blot analysis or a promoter/reporter-based whole cell assay.

In another aspect of the present invention, IκBα kinase complex or IκBα kinase may be used for phosphorylating IκBα (or a derivative or variant thereof) so as to render it a target for ubiquitination and subsequent degradation. IκBα may be phosphorylated in vitro by incubating IκBα kinase complex or IκBα kinase with IκBα in a suitable buffer for 30 minutes at 30° C. In general, about 0.01 μg to about 9 μg of IκBα kinase complex is sufficient to phosphorylate from about 0.5 μg to about 2 μg of IκBα. Phosphorylated substrate may then be purified by binding to GSH-sepharose and washing. The extent of substrate phosphorylation may generally be monitored by adding [γ-$^{32}$P]ATP to a test aliquot, and evaluating the level of substrate phosphorylation as described herein.

An IκBα kinase complex, component thereof, modulating agent and/or polynucleotide encoding a component and/or modulating agent may also be used to modulate NF-κB activity in a patient. As used herein, a "patient" may be any mammal, including a human, and may be afflicted with a disease associated with IκBα kinase activation and the NF-κB cascade, or may be free of detectable disease. Accordingly, the treatment may be of an existing disease or may be prophylactic. Diseases associated with the NF-κB cascade include inflammatory diseases, autoimmune diseases, cancer and viral infection.

Treatment may include administration of a IκBα kinase complex, a component thereof and/or an agent which modulates IκBα kinase activity. For administration to a patient, one or more such compounds are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Alternatively, a pharmaceutical composition may comprise a polynucleotide encoding a component of an IκBα kinase complex and/or a modulating agent (such that the component and/or modulating agent is generated in situ) in combination with a physiologically acceptable carrier. In such pharmaceutical compositions, the polynucleotide may be present within any of a variety of delivery systems known to those of ordinary skill in the art, including nucleic acid, bacterial and viral expression systems, as well as colloidal dispersion systems, including liposomes. Appropriate nucleic acid expression systems contain the necessary polynucleotide sequences for expression in the patient (such as a suitable promoter and terminating signal). DNA may also be "naked," as described, for example, in Ulmer et al., *Science* 259:1745–1749 (1993).

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific). For example, retroviral vectors can be made target specific by inserting a nucleotide sequence encoding a sugar, a glycolipid, or a protein. Targeting may also be accomplished using an antibody, by methods known to those of ordinary skill in the art.

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) $\Psi 2$, PA317 and PA12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques* 6:882, 1988).

The targeting of liposomes can be classified based on anatomical and mechanistic factors. Anatomical classification is based on the level of selectivity and may be, for example, organ-specific, cell-specific, and/or organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Routes and frequency of administration, as well doses, will vary from patient to patient. In general, the pharmaceutical compositions may be administered intravenously, intraperitoneally, intramuscularly, subcutaneously, intracavity or transdermally. Between 1 and 6 doses may be administered daily. A suitable dose is an amount that is sufficient to show improvement in the symptoms of a patient afflicted with a disease associated with the NF-$\kappa$B cascade. Such improvement may be detected by monitoring inflammatory responses (e.g., edema, transplant rejection, hypersensitivity) or through an improvement in clinical symptoms associated with the disease. In general, the amount of modulating agent present in a dose, or produced in situ by DNA present in a dose, ranges from about 1 $\mu$g to about 200 mg per kg of host. Suitable dose sizes will vary with the size of the patient, but will typically range from about 10 mL to about 500 mL for 10–60 kg animal.

In another aspect, the present invention provides methods for detecting the level of stimulus-inducible I$\kappa$B$\alpha$ kinase activity in a sample. The level of I$\kappa$B$\alpha$ kinase activity may generally be determined via an immunokinase assay, in which I$\kappa$B$\alpha$ kinase complex is first immunoprecipitated with an antibody that binds to the complex. The immunoprecipitated material is then subjected to a kinase assay as described herein. Substrate specificity may be further evaluated as described herein to distinguish the activity of a stimulus-inducible I$\kappa$B$\alpha$ kinase complex from other kinase activities.

The present invention also provides methods for detecting the level of I$\kappa$B$\alpha$ kinase complex, or a component thereof, in a sample. The amount of I$\kappa$B$\alpha$ kinase complex, I$\kappa$B$\alpha$ kinase or nucleic acid encoding I$\kappa$B$\alpha$ kinase, may generally be determined using a reagent that binds to I$\kappa$B$\alpha$ kinase, or to DNA or RNA encoding a component thereof. To detect nucleic acid encoding a component, standard hybridization and/or PCR techniques may be employed using a nucleic acid probe or a PCR primer. Suitable probes and primers may be designed by those of ordinary skill in the art based on the component sequence. To detect I$\kappa$B$\alpha$ kinase complex or a component thereof, the reagent is typically an antibody, which may be prepared as described below.

There are a variety of assay formats known to those of ordinary skill in the art for using an antibody to detect a protein in a sample. See, e.g., Harlow and Lane, *Antibodies: A Laboratory Manual*, Cold Spring Harbor Laboratory, 1988. For example, the antibody may be immobilized on a solid support such that it can bind to and remove the protein from the sample. The bound protein may then be detected using a second antibody that binds to the antibody/protein complex and contains a detectable reporter group. Alternatively, a competitive assay may be utilized, in which protein that binds to the immobilized antibody is labeled with a reporter group and allowed to bind to the immobilized antibody after incubation of the antibody with the sample. The extent to which components of the sample inhibit the binding of the labeled protein to the antibody is indicative of the level of protein within the sample. Suitable reporter groups for use in these methods include, but are not limited to, enzymes (e.g., horseradish peroxidase), substrates, cofactors, inhibitors, dyes, radionuclides, luminescent groups, fluorescent groups and biotin.

Antibodies encompassed by the present invention may be polyclonal or monoclonal, and may bind to I$\kappa$B$\alpha$ kinase complex and/or one or more components thereof. Preferred antibodies are those antibodies that inhibit or block I$\kappa$B$\alpha$ kinase activity in vivo and within an in vitro assay, as described above. Other preferred antibodies are those that bind to IκBα. As noted above, antibodies and other agents having a desired effect on IκBα kinase activity may be administered to a patient (either prophylactically or for treatment of an existing disease) to modulate the phosphorylation of IκBα in vivo.

Antibodies may be prepared by any of a variety of techniques known to those of ordinary skill in the art (see, e.g., Harlow and Lane, *Antibodies: A Laboratory Manual*, Cold Spring Harbor Laboratory, 1988). In one such technique, an immunogen comprising the protein of interest is initially injected into a suitable animal (e.g., mice, rats, rabbits, sheep and goats), preferably according to a predetermined schedule incorporating one or more booster immunizations, and the animals are bled periodically. Polyclonal antibodies specific for the protein may then be purified from such antisera by, for example, affinity chromatography using the protein coupled to a suitable solid support.

Monoclonal antibodies specific for a IκBα kinase complex or a component thereof may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (i.e., reactivity with the complex and/or component of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

In a related aspect of the present invention, kits for detecting the level of IκBα kinase complex, IκBα kinase, nucleic acid encoding IκBα kinase and/or IκBα kinase activity in a sample are provided. Any of a variety of samples may be used in such assays, including eukaryotic cells, bacteria, viruses, extracts prepared from such organisms and fluids found within living organisms. In general, the kits of the present invention comprise one or more containers enclosing elements, such as reagents or buffers, to be used in the assay.

A kit for detecting the level of IκBα kinase complex, IκBα kinase or nucleic acid encoding IκBα kinase, typically contains a reagent that binds to the compound of interest. To detect nucleic acid encoding IκBα kinase, the reagent may be a nucleic acid probe or a PCR primer. To detect IκBα kinase complex or IκBα kinase, the reagent is typically an antibody. Such kits also contain a reporter group suitable for direct or indirect detection of the reagent (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

In yet another aspect, IκBα kinase complex may be used to identify one or more native upstream kinases (i.e., kinases that phosphorylate and activate IκBα kinase complex in vivo) or other regulatory molecules that affect IκBα kinase activity (such as phosphatases or molecules involved in ubiquitination), using methods well known to those of ordinary skill in the art. For example, IκBα kinase components may be used in a yeast two-hybrid system to identify proteins that interact with such components. Alternatively, an expression library may be screened for cDNAs that phosphorylate IκBα kinase or a component thereof.

The following Examples are offered by way of illustration and not by way of limitation.

EXAMPLES

Example 1

Preparation of IκBα Kinase Complex

This Example illustrates the preparation and characterization of an IκBα kinase complex.

HeLa S3 cells were grown to a cell density of approximately $0.6 \times 10^6$/mL, concentrated 10 fold and induced with TNFα (30 ng/mL) for seven minutes. Two volumes of ice-cold PBS containing phosphatase inhibitors (10 mM sodium fluoride, 0.3 mM sodium orthovanadate and 20 mM β-glycerophosphate) were then added. The cells were spun down, washed once with ice-cold PBS containing phosphatase inhibitors and snap frozen.

Standard protocols were then used to prepare cytoplasmic and nuclear extracts. More specifically, the frozen HeLa S3 cell pellet was quick-thawed at 37° C., resuspended in 2 volumes of ice-cold Hypotonic Lysis Buffer (20 mM Tris pH 8.0, 2 mM EDTA, 1 mM EGTA, 10 mM β-glycerophosphate, 10 mM NaF, 10 mM PNPP, 0.3 mM $Na_2VO_4$, 5 sodium pyrophosphate, 1 mM benzamidine, 2 mM PMSF, 10 μg/mL aprotinin, 1 μg/mL leupeptin and 1 μg/mL pepstatin), and left to incubate on ice for 30 min. The swollen cells were then dounced 30 times using a tight pestle and the nuclei were pelleted at 10,000 rpm for 15 minutes at 4° C. The supernatant was clarified via ultracentrifugation (50,000 rpm for 1 hour at 4° C.) to generate the final cytoplasmic extract. The nuclear/membrane pellet was resuspended in an equal volume of High Salt Extraction Buffer (20 mM Tris pH 8.0, 0.5M NaCl, 1 mM EDTA, 1 mM EGTA, 0.25% Triton X-100, 20 mM β-glycerophosphate, 10 mM NaF, 10 mM PNPP, 0.3 mM $Na_2VO_4$, 1 mM benzamidine, 1 mM PMSF, 1 mM DTT, 10 μg/mL aprotinin, 1 μg/mL leupeptin and 1 μg/mL pepstatin) and allowed to rotate at 4° C. for 30 minutes. Cell debris was removed via centrifugation at 12,500 rpm for 30 minutes at 4° C. and the resulting supernatant was saved as the nuclear/membrane extract.

These extracts were then independently subjected to a series of chromatographic steps (shown in FIG. 1) using a Pharmacia FPLC system (Pharmacia Biotech, Piscataway, N.J.):

(1) Q Sepharose (Pharmacia Biotech, Piscataway, N.J.)—the column as run with a linear gradient starting with 0.0M NaCl Q Buffer (20 mM Tris pH 8.0, 0.5 mM EDTA, 0.5 mM EGTA, 0.025% Brij 35, 20 mM β-glycerophosphate, 10 mM NaF, 0.3 mM $Na_2VO_4$, 1 Mm benzamidine, 1 mM PMSF, 2 mM DTT, 1 μg/mL aprotinin, 1 μg/mL leupeptin and 1 μg/mL pepstatin) and ending with 0.5M NaCl Q Buffer. The IκBα kinase activity eluted between 0.25 and 0.4 M NaCl.

(2) Gel Filtration HiLoad 16/60 Superdex 200) (Pharmacia Biotech, Piscataway, N.J.)—the column was run with Gel Filtration Buffer (20 mM Tris pH 8.0, 150 mM NaCl, 1 mM EDTA, 1 mM EGTA, 0.05% Brij 35, 20 mM β-glycerophosphate, 10 mM NaF, 0.3 mM $Na_2VO_4$, 1 mM benzamidine, 1 mM PMSF, 1 mM DTT, 10 μg/mL aprotinin, 1 μg/mL leupeptin and 1 μg/mL pepstatin). The peak IκBα kinase activity eluted at 40–48 mL, which corresponds to a molecular weight of 731 kD to 623 kD.

(3) HR 5/5 Mono Q (Pharmacia Biotech, Piscataway, N.J.)—the column was run with a linear gradient starting with 0.0M NaCl Q Buffer and ending with 0.5M NaCl Q Buffer (without Brij detergent to prepare sample for Phenyl Superose column). The IκBα kinase activity eluted between 0.25 and 0.4 M NaCl.

(4) HR Phenyl Superose (Pharmacia Biotech, Piscataway, N.J.)—the column was run with a linear gradient of 1.0M to 0.0M ammonium sulfate in Phenyl Superose Buffer (20 mM Tris pH 8.0, 0.25 EDTA, 1 mM EGTA, 20 mM β-glycerophosphate, 10 mM NaF, 0.1 mM $Na_2VO_4$, 1 mM benzamidine, 1 mM PMSF, 1 mM DTT, 10 μg/mL aprotinin, 1 μg/mL leupeptin and 1 μg/mL pepstatin). The IκBα kinase activity eluted between 0.35 and 0.2 M ammonium sulfate.

(5) Gel Filtration Superdex 200 HR 10/30 (Pharmacia Biotech, Piscataway, N.J.)—the column was run with Gel Filtration Buffer (see (2), above). The peak of activity eluted at 8–10 mL, which corresponds to a molecular weight of 720 kD to 600 kD.

(6) HR 5/5 Mono Q—the column was run as in (3) above except that the 0.05% Brij 35 was included in all Q buffers.

IκBα kinase activity, with similar substrate specificity and molecular weight, was isolated from both the cytoplasmic and nuclear/membrane extracts.

At each step of the fractionation, IκBα kinase activity was monitored using an in vitro assay. The assay was performed by combining 2 μg of the respective IκBα substrate (GST-IκBα 1–54 (wildtype) or GST-IκBα (S32/36 to T), as described below) with 3–5 μL chromatographic fraction and 20 μL of Kinase Assay Buffer (20 mM HEPES pH 7.4, 10 mM $MgCl_2$, 10 mM $MnCl_2$, 20 mM NaCl, 1 mM DTT, 20 mM PNPP, 20 μM ATP, 20 mM β-glycerophosphate, 10 mM NaF, 0.1 mM $Na_2VO_4$, 1 mM benzamidine, 1 mM PMSF) containing $\gamma^{32}P$-ATP, and incubating for 30 minutes at 30° C. The kinase reaction was terminated by adding 8 μL of 6× SDS-PAGE sample buffer. The entire sample was run on a 12% polyacrylamide gel, dried and subjected to autoradiography.

IκBα substrates for use in the above assay were prepared using standard techniques (see Haskill et al., *Cell* 65:1281–1289, 1991). The GST-IκBα 1–54 (wildtype) or GST-IκBα (S32/36 to T) substrates were prepared using standard techniques for bacterially expressed GST-protein. Bacterial cells were lysed, GST proteins were purified via binding to GST-agarose beads, washed several times, eluted from the beads with glutathione, dialyzed against 50 mM NaCl Kinase Assay Buffer and stored at −80° C.

The TNFα-inducibility of IκBα kinase activity was initially evaluated by Western blot analysis of the levels of IκBα in HeLa S3 cytoplasmic extracts following gel filtration. IκBα was assayed by running 18 μL of the gel filtration fractions on 10% SDS PAGE, transferring to Nitrocellulose Membrane (Hybond-ECL, Amersham Life Sciences, Arlington Height, Ill.) using standard blotting techniques and probing with anti-IκBα antibodies (Santa Cruz Biotechnology, Inc., Santa Cruz, Calif.). TNFα-inducibility was evaluated by comparing the level of IκBα in cells that were (FIG. 2B) and were not (FIG. 2A) exposed to TNFα (30 ng/mL for seven minutes, as described above).

Figure 3A:
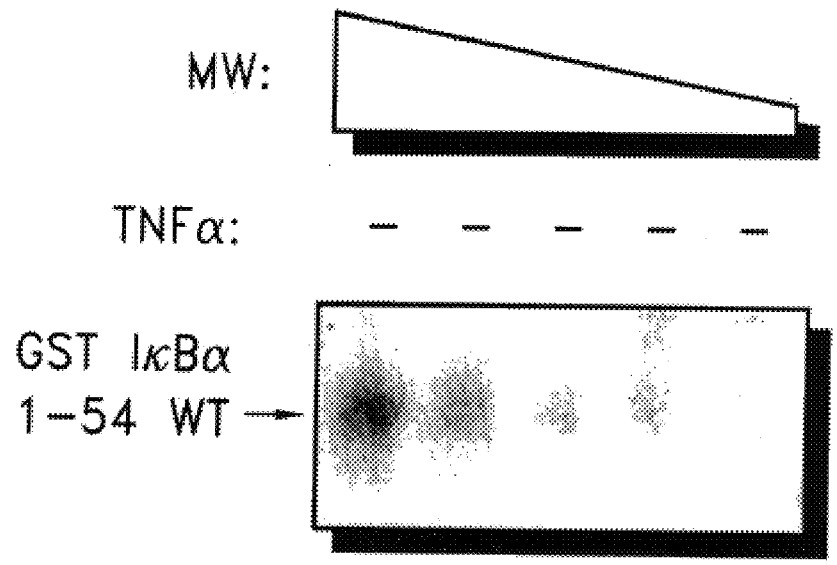
FIGS. 3A and 3B are autoradiograms depicting the results of an in vitro kinase assay in which the ability of the above cell extracts to phosphorylate the N-terminal portion of IκBα was evaluated.
Figure 3B:
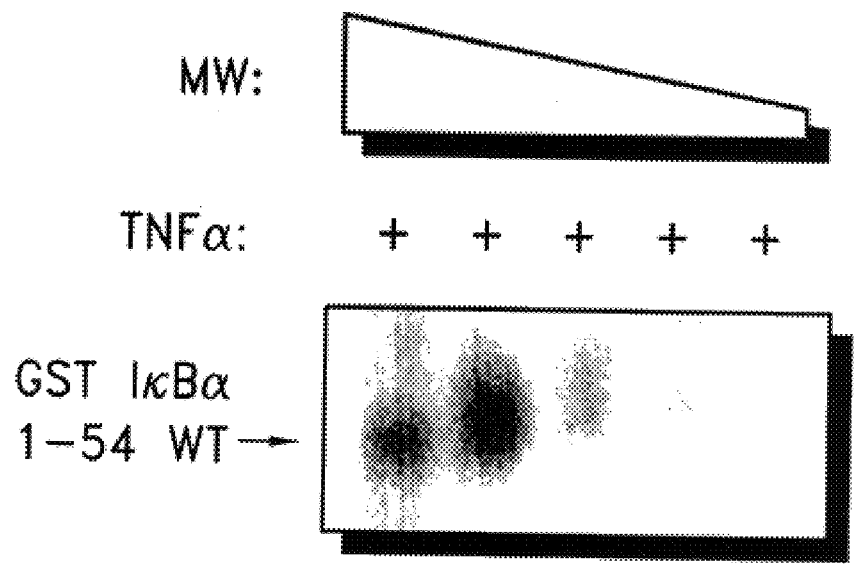

The IκBα kinase activity of these cytoplasmic extracts was evaluated using the kinase assay described above. As shown in FIG. 3B, the extract of TNFα-treated cells phosphorylated GST-IκBα 1–54 (wildtype), while the untreated cell extract showed significantly lower levels of IκBα kinase activity (FIG. 3A).

Figure 4A:
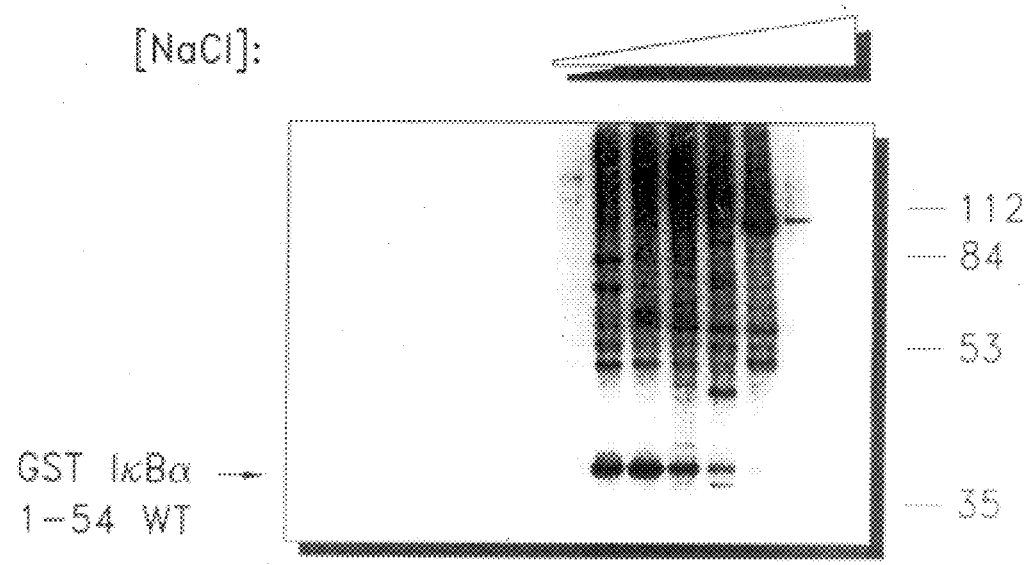
FIGS. 4A and 4B are autoradiograms depicting the results of an in vitro kinase assay using a cytoplasmic extract of TNFα-treated HeLa S3 cells, where the extract is subjected to Q Sepharose fractionation. The substrate was the truncated IκBα (residues 1 to 54), with FIG. 4A showing the results obtained with the wild type IκBα sequence and FIG. 4B presenting the results obtained using a polypeptide containing threonine substitutions at positions 32 and 36.
Figure 4B:
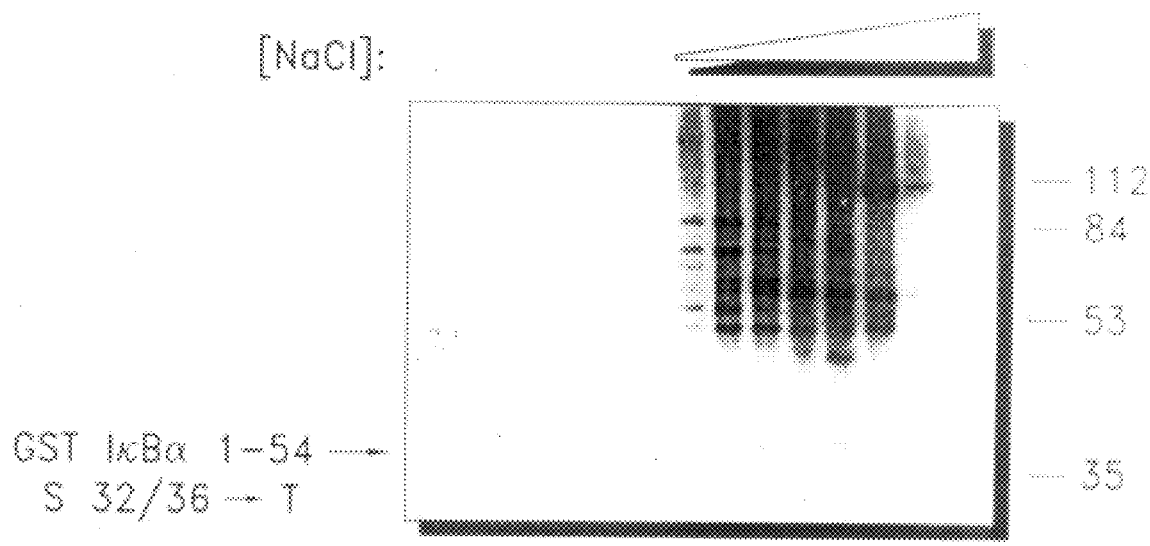

Cytoplasmic extracts of TNFα-treated HeLa S3 cells (following Q Sepharose fractionation) were also subjected to in vitro kinase assays, using the N-terminal portion of IκBα (residues 1 to 54) as substrate. With the wild type substrate, phosphorylation of GST-IκBα 1–54 was readily apparent (FIG. 4A). In contrast, substrate containing threonine substitutions at positions 32 and 36 was not phosphorylated (FIG. 4B).

Figure 5A:
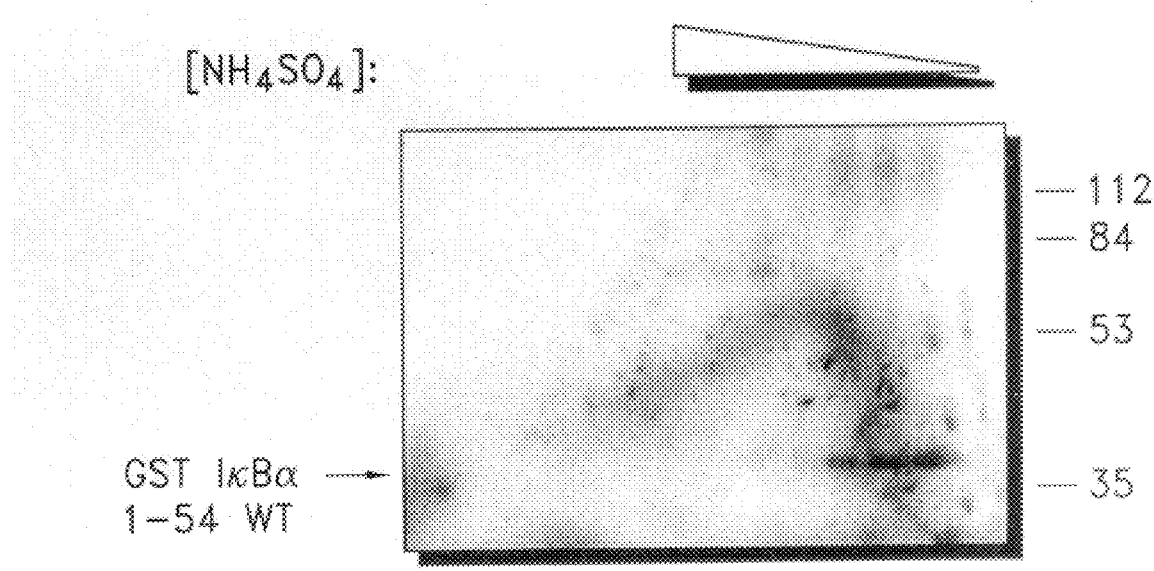
FIGS. 5A and 5B are autoradiograms depicting the results of an in vitro kinase assay using a cytoplasmic extract of TNFα-treated HeLa S3 cells, where the extract was subjected in series to chromatographic fractionation by Q Sepharose, Superdex 200, Mono Q Sepharose and Phenyl Superose. The substrate was the truncated IκBα (residues 1 to 54), with FIG. 5A showing the results obtained with the wild type IκBα sequence and FIG. 5B presenting the results obtained using a polypeptide containing threonine substitutions at positions 32 and 36.
Figure 5B:
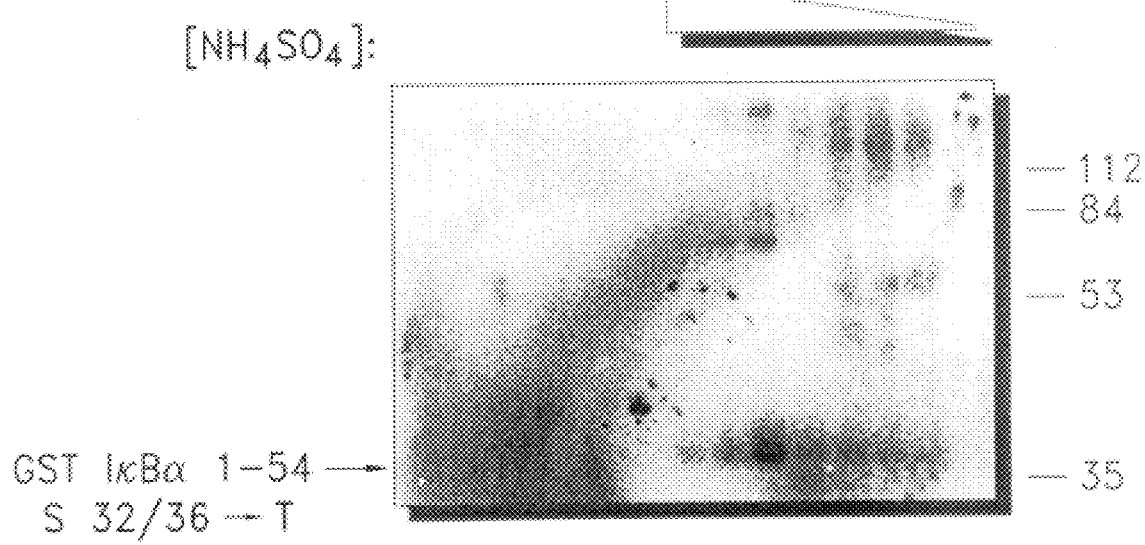

Following chromatographic fractionation by Q Sepharose, Superdex 200, MonoQ Sepharose and Phenyl Superose, in vitro kinase assay showed substantial purification of the IκBα kinase activity (FIG. 5A). Further purification of the IκBα kinase was achieved by passing the sample over, in series, an analytical Superdex 200 and Mono Q HR 5/5, resulting in 8 major protein bands as determined by silver staining. As before, the use of substrate containing threonine substitutions at positions 32 and 36 markedly reduced the phosphorylation (FIG. 5B). These results demonstrate the purification of a stimulus-inducible IκBα kinase complex, which specifically phosphorylates serine residues at positions 32 and 36 of IκBα without the addition of exogenous factors.

Example 2

Immunoprecipitation of IκBα Kinase Complex Using Anti MKP-1 Antibodies

This Example illustrates the immunoprecipitation of IκBα kinase activity from cytoplasmic extracts prepared from TNF-α-treated cells (30 μg/mL, 7 minutes) following gel filtration.

Twenty μL of gel filtration fraction #6 (corresponding to about 700 kD molecular weight) and 1 μg purified antibodies raised against MKP-1 (Santa Cruz Biotechnology, Inc., Santa Cruz, Calif.) were added to 400 μL of ice cold Pull Down Buffer (20 mM Tris pH 8.0, 250 mM NaCl, 0.05% NP-40, 3 mM EGTA, 1 mM PMSF, 10 μg/mL aprotinin, 1 μg/mL leupeptin and 1 μg/mL pepstatin). The sample was gently rotated for 1 hour at 4° C., at which time 40 μL of protein A-agarose beads (50:50 slurry, Santa Cruz Biotechnology, Inc., Santa Cruz, Calif.) was added. The sample was then rotated for an additional 1.5 hours at 4° C. The protein A-agarose beads were pelleted at 3,000 rpm for 2 minutes at 4° C. and the pellet was washed three times with ice cold Pull Down Buffer (800 μL per wash).

The pellet was subjected to the standard in vitro IκBα kinase assay (as described above) using either 2 μg GST-IκBα1–54 (wildtype) or 2 μg GST-IκBα1–54 (S32/36 to T) as the substrate.

The results, shown in FIG. 6, demonstrate that antibodies directed against MKP-1 immunoprecipitate the stimulus-inducible IκBα kinase activity. The substrate specificity of this IκBα kinase activity corresponds to what has been described in vivo (strong phosphorylation of the GST-IκBα1–54 (wildtype) and no phosphorylation using GST-IκBα1–54 (S32/36 to T).

Example 3

Absence of Free Ubiquitin in Purified IκBα Kinase Complex

This example illustrates the absence of detectable free ubiquitin with a IκBα kinase complex prepared as in Example 1. Standard western blot procedures were performed (Amersham Life Science protocol, Arlington Heights, Ill.). 100 ng ubiquitin, 10 ng ubiquitin and 20 µl purified IκBα kinase complex was subjected to 16% Tricine SDS-PAGE (Novex, San Diego, Calif.), transferred to Hybond ECL Nitrocellulose membrane (Amersham Life Science, Arlington Heights, Ill.), and probed with antibodies directed against ubiquitin (MAB1510 Chemicon, Temecula, Calif.). The results are shown in FIG. 7. Free ubiquitin could not be detected in our purified IκBα kinase preparation (even at very long exposures). The complexes described herein do not require addition of endogenous ubiquitin to detect IκBα kinase activity, nor is free ubiquitin a component in the purified IκBα kinase preparations of the present invention.

From the foregoing, it will be appreciated that, although specific embodiments of the invention have been described herein for the purpose of illustration, various modifications may be made without deviating from the spirit and scope of the invention.

We claim:

1. A stimulus-inducible IκBα kinase complex, wherein said complex has a molecular weight of about 700 kD, as determined by gel filtration chromatography, and wherein said complex is capable of specifically phosphorylating IκBα at residues S32 and/or 36 in vitro without the addition of ubiquitin.

2. A complex according to claim 1 wherein said complex is derived from a human tissue or cell line.

* * * * *